US006319690B1

(12) United States Patent
Little et al.

(10) Patent No.: US 6,319,690 B1
(45) Date of Patent: Nov. 20, 2001

(54) PREPARATION AND USE OF GENE BANKS OF HUMAN ANTIBODIES ("HUMAN-ANTIBODY LIBRARIES")

(75) Inventors: Melvyn Little, Neckargemünd; Frank Berthold Breitling, Wiesloch; Thomas Seehaus, Heppenheim; Stefan Dübel, Heidelberg; Iris Klewinghaus, Mannheim, all of (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/057,430

(22) Filed: May 6, 1993

Related U.S. Application Data

(63) Continuation of application No. 07/648,522, filed on Jan. 30, 1991, now abandoned.

(30) Foreign Application Priority Data

Feb. 1, 1990 (DE) ................................. 40 02 898
Feb. 9, 1990 (DE) ................................. 40 03 881

(51) Int. Cl.$^7$ ................................. C12N 15/00
(52) U.S. Cl. ............... 435/69.6; 435/69.1; 435/70.2; 530/387.1
(58) Field of Search ............ 435/6, 69.1, 172.3, 435/71.1, 172.1, 70.2, 69.6; 530/387.1; 935/80, 81; 536/24.33

(56) References Cited

FOREIGN PATENT DOCUMENTS

WO 90/14430   11/1990  (WO) .
WO 91/10737    7/1991  (WO) .

OTHER PUBLICATIONS

L. Riechmann et al. "Crystallization of an Anti–2,2,6, 6–Tetramethyl–1–piperidinyloxy–dinitrohpenyl Monoclonal Antibody Fab Fragment With and Without Bound Hapten," J. Mol. Biol. 203:829–830 (1988).

D. Straus et al., "Chicken Triosephosphate Isomerase Complements an *Escherichia coli* Deficiency," Proc. Natl. Acad. Sci. 82:2014–2013 (1985).

E. Amann et al., "ATG Vectors' for Regulated High–Level Expression of Cloned Genes in *Escherichia coli*," Gene 40:183–190 (1985).

J. Wehland et al., "Amino Acid Sequence Requirements in the Epitope Recognized by the α–Tubulin–Specific Rat Monoclonal Antibody YL 1/2," EMBO Journal 3,6:1295–1300 (1984).

W.D. Huse et al., "Generation of Large Combinatorial Library of the Immunoglobulin Repertoire in Phage Lambda," Science 246:1273–1281 (1989).

E.S. Ward et al., "Binding Activities of a Repertoire of Single Immunoglobulin Variable Domains Secreted From *Escherichia coli*," Nature 341:544–546 (1989).

L. Sastry et al., "Cloning of the Immunological Repertoire in *Escherichia coli* for Generation of Monoclonal Catalytic Antibodies: Construction of a Heavy Chain Variable Region–Specific cDNA Library," Proc. Natl. Acad. Sci. 86:5728–5732 (1989).

R. Orlandi et al., "Cloning Immunoglobulin Variable Domains for Expression by the Polymerase Chain Reaction," Proc. Natl. Acad. Sci. 86:3833–3837 (1989).

A. Skerra et al., "Assembly of a Functional Immunoglobulin $F_v$ Fragment in *Escherichia coli*," Science 240:1038–1041 (1988).

M. Better et al., "*Escherichia coli* Secretion of an Active Chemeric Antibody Fragment," Science 240:1041–1043 (1988).

M.J. Zoller et al., "Oligonucleotide–Directed Mutagenesis of DNA Fragments Cloned into M13 Vectors," Method in Enzymology 100:468–501 (1983).

G. Winter et al., "Man–made Antibodies," Nature, 349: 293–299 (1991).

Kimball *Introduction to Immunology*, $2^{nd}$ Ed. MacMillan Publ. Co., NY. NY., 1986.*

* cited by examiner

*Primary Examiner*—Sheela Huff
*Assistant Examiner*—Larry R. Helms
(74) *Attorney, Agent, or Firm*—Finnegan, Henderson, Farabow, Garrett and Dunner, L.L.P.

(57) ABSTRACT

The invention relates to the preparation and use of gene banks of human antibodies (Ab). Starting from a mixture of human B-lymphocytes, their mRNA is translated into the cDNA using oligo-dT primers. Subsequently, an amplification of the Ab-specific cDNA by means of polymerase chain reaction (PCR) takes place using suitable oligonucleotide primer sequences. Expression of this amplified Ab-specific cDNA in a bacterial expression vector, e.g. the vector pFMT described below, in *E. coli* thus makes available a human-antibody library with a comprehensive repertoire for screening selected antigens in vitro.

16 Claims, 1 Drawing Sheet

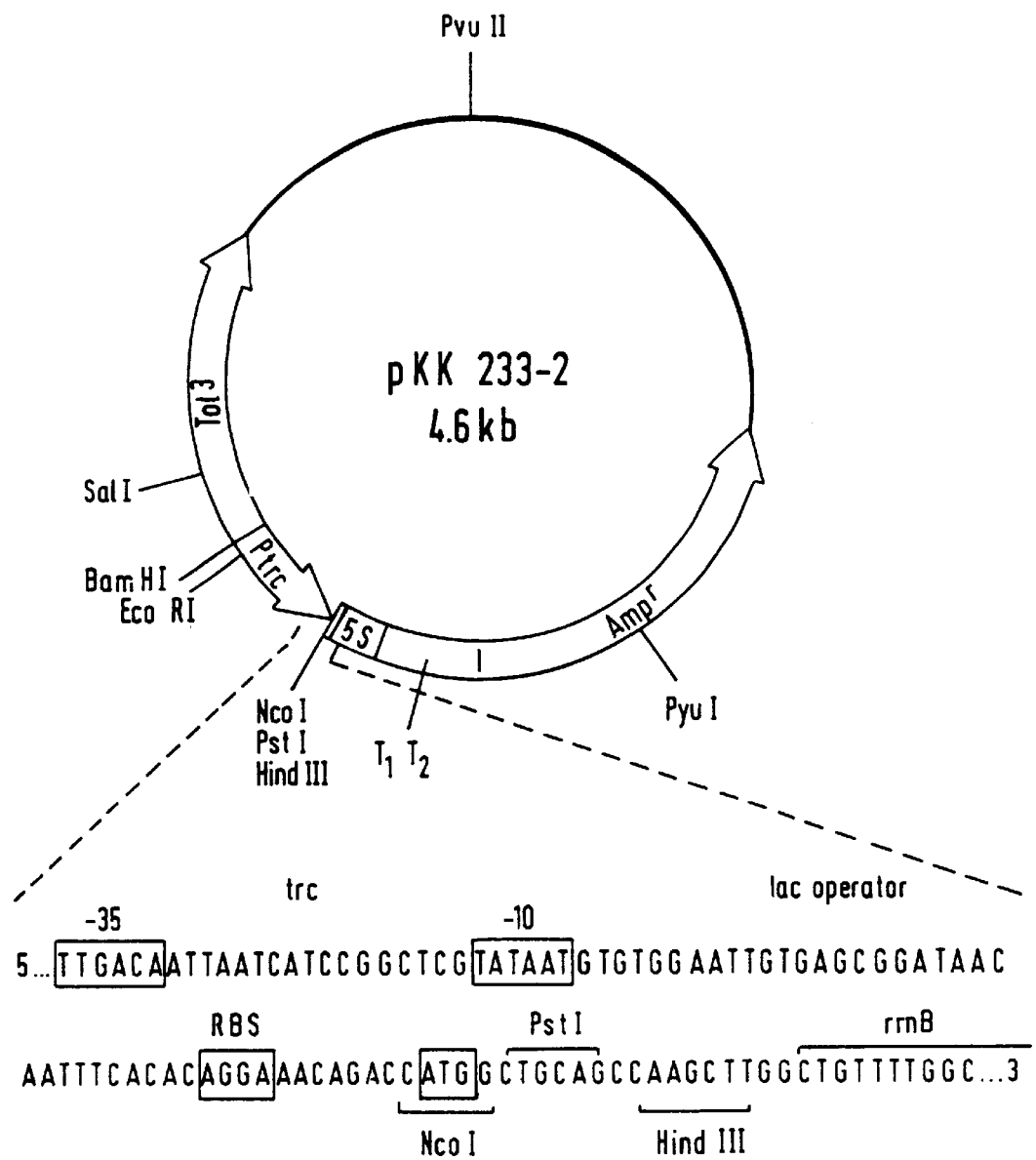

PREPARATION AND USE OF GENE BANKS OF HUMAN ANTIBODIES ("HUMAN-ANTIBODY LIBRARIES")

This application is continuation, of application Ser. No. 07/648,522, filed Jan. 30, 1991, now abandoned.

The invention relates to the preparation and use of gene banks of human antibodies (Ab). Starting from a mixture of human B-lymphocytes, their mRNA is translated into cDNA using oligo-dT primers. Subsequently, an amplification of the Ab-specific cDNA by means of polymerase chain reaction (PCR) takes place using suitable oligonucleotide primer sequences. Expression of this amplified Ab-specific cDNA in a bacterial expression vector, e.g. the vector pFMT described below, in *E. coli* thus makes available a human-antibody library with a comprehensive repertoire for screening selected antigens in vitro.

The human or mammalian immune system comprises an estimated number of between $10^6$ and $10^8$ different antibodies. This number of antibodies seems to be sufficient to cause an immune reaction of the body both against all naturally occurring antigens and against artificial antigens. If it is furthermore taken into account that often several antibodies react with the same antigen, the repertoire of antibodies that are really different would be rather in the region from $10^6$ to $10^7$.

Up to now specific antibodies have always been obtained starting from an immunization with the particular antigen, for example injection of the antigen into the body or in vitro incubation of spleen cells with this antigen. In the case of polyclonal antibodies, the immunoglobulins can then be isolated from the serum and the specific antibodies can be isolated therefrom, e.g. by absorption methods. Monoclonal antibodies are isolated from the cell supernatants or from the cell lysate of spleen tumor cells (hybridoma cells) which have been fused with individual B lymphocytes and cloned. The abovementioned methods are unsuitable in particular for the preparation of specific human antibodies or human monoclonal antibodies.

The present invention therefore has the object of developing a generally usable process for generating specific human monoclonal antibodies (huMAbs) or parts of antibodies, which contain the antigen binding site.

It has been found that the desired huMAbs or parts thereof which contain the variable, antigen binding domain can be isolated from gene banks of human immunoglobulins. First of all, starting from a mixture of nonactivated human B-lymphocytes, their mRNA was isolated and translated into cDNA with the aid of oligo-dT primers (SEQ ID NOS 1–10). A specific amplification of the population of antibody cDNAs within the resulting cDNA pool was achieved by using PCR. For this purpose certain oligonucleotide primers which are homologous to conserved sequences at both ends of the antibody cDNA were used (see below and examples). The design of the primer (SEQ ID NOS 4–11) for the reverse reaction for the synthesis of the noncoding strand of the DNA of the heavy chains is based on IgM sequences (subclass III, since this comprises most of the IgM sequences). IgM molecules occur more often in non-activated B-lymphocytes than all other immunoglobulin classes. In contrast, IgG sequences predominate in activated B-lymphocytes whose repertoire of different antibodies is very much smaller. An IgG library would additionally entail the danger of one or a few particularly strongly expressed IgGs dominating the library.

Up to 30 amplification cycles were, advantageously, carried out. The oligonucleotide primers contain suitable restriction sites for inserting the amplified DNA e.g. into the antibody expression plasmid pFMT (see below).

This expression plasmid makes possible the expression of antibody cDNA and subsequent secretion of the expression products in bacteria (*E.coli*). The antibody operon of the plasmid contains the sequences (SEQ ID NOS 26–29) of the variable parts of both the heavy and light chain of an antibody. Suitable leader sequences from the amino terminal part of a bacterial protein makes secretion of the antibody parts possible. The leader sequences (SEQ ID NOS 12–15) are cleaved off by a bacterial enzyme during the secretion. During the secretion of the antibody cDNA products, the light and heavy chains of the antibody (with or without an adjacent constant domain) become associated. This results in the formation of an antibody or antibody fragment which, in either case, contains a functional antigen binding site. Similar constructs for individual antibodies have also been described by other authors (Better et al. (1988), Science 240, 1041, and Skerras & Plückthun (1988), Science 240, 1038).

It is true that the amplification of DNA coding for the variable parts of antibodies has been described by other authors (Orlandi et al. (1989), Proc. Natl. Acad. Sci. 86, 3833; Sastry et al., (1989) Proc. Natl. Acad. Sci. 86, 5728; Ward et al. (1989), Nature 341, 544); Huse et al. (1989), Science 246, 275). In this case however, the mRNA which, inter alia, also codes for antibodies was isolated from hybridoma cells or spleen lymphocytes after treatment with a certain antigen. For this reason primer sequences which are based only on IgG sequences were also used there. This is, of course, an advantage if as many antibody DNA clones as possible which are derived from activated lymphocytes are sought. With primers from IgG sequences, the chances of finding clones which contain DNA coding for antibodies against the injected antigen are much higher. It has to be added that in the foregoing papers murine and therefore nonhuman antibody DNA was synthesized and, additionally with exclusion of regions of the lambda chain, amplified.

The present invention, in contrast, uses primer sequences which are homologous to the sequences in the constant domains of IgM cDNA. This is the best way of implementing the invention, i.e. making available a very large choice of antibodies, namely the whole antibody repertoire, in the form of a library. The expression in, preferably, *E. coli* then results in the desired human-antibody library in which the desired human antibodies or antibody parts are found by means of screening bacterial clones using the selected antigen.

Oligonucleotide primers suitable for amplification are compiled in Tab. 1 (SEQ ID NOS 1–11). The positions of the abovementioned primers on the $\mu$, kappa and lambda chains are shown in the form of a diagram in Tab. 2. The molecular biological constructions of, amongst others, the expression vector, i.e. the antibody expression plasmid PFMT, are described in detail in the examples below.

The invention therefore relates to human-antibody libraries, prepared by transcription of the mRNA from nonactivated (peripheral) human B-lymphocytes by means of oligo-dT primers, subsequent amplification by PCR using primers containing sequences which are homologous to conserved regions of the IgM cDNA, and subsequent incorporation into suitable expression plasmids for the expression in microorganisms, preferably in the expression vector pFMT for the expression in *E. coli*. In a preferred embodiment an additional sequence is incorporated which codes for a marker peptide, e.g. a TAG sequence so that the expression products can be detected in a simple manner using established monoclonal antibodies against the marker peptide (Wehland et al., (1984), EMBO J. 3, 1295).

The invention also relates to the use of abovementioned human-antibody libraries for isolating desired human antibodies or parts of antibodies containing a functional antigen binding site by screening using selected antigens, and to a process for isolating the said human antibodies or their antigen-binding parts, and also to a process for preparing the said human-antibody libraries.

The invention also relates to expression vectors having the properties of the antibody expression plasmid pFMT.

The examples below further illustrate the invention without restricting it. Finally, the invention is also contained in the patent claims.

EXAMPLES

Example 1
Preparation of an Antibody Expression Vector

The plasmid pKK233-2 (Deutsche Sammlung Von Mikroorganismen (DSMZ), Braunschweig, Germany, Accession number DSM 14209; Amann and Brosius, (1985) Gene 40,183 and Straus and Gilbert, (1985) Proc. Natl. Acad. Sci. 82, 2014) was chosen as base vector for the construction of the antibody expression vector (FIG. 1).

Before the incorporation of the antibody operon, the plasmid was cut with SalI and BamHI, the ends were filled in with Klenow polymerase and ligated. By doing so, the two restriction sites and the DNA between them were removed. Additionally, the plasmid was cleaved with HindIII, the ends were filled in with Klenow polymerase and ligated using BamHI linkers. By this procedure, the HindIII restriction site was removed and a BamHI site inserted. The antibody DNA was inserted into this modified plasmid. A diagrammatic route for construction of the antibody operon which codes for a bicistronic antibody mRNA is shown in Tab. 3. In order to make possible the secretion of the antibody, the leader sequence (SEQ ID NOS. 12–15) of the bacterial enzyme pectate lyase was used. The leader sequence of this enzyme has already been used for the expression and secretion of a chimeric murine/human antibody (Fab fragment, Better et al., loc. cit.), and of the variable part of a "humanized" antibody (Ward et al., loc. cit.; Huse et al., loc. cit.). DNA for the first leader sequence (SEQ ID NOS. 12–13) ($P_1$ upstream of the heavy chain), and the sequence for a second ribosome binding site (RBS) and a second leader sequence (SEQ ID NOS. 14–15) ($P_2$ upstream of the light chain) were synthesized from several oligonucleotides (Tab. 4) (SEQ ID NOS. 16–23).

Antibody cDNAs which code for the variable regions of the heavy and light chains of a human antibody (HuVhlys or HuVllys; Riechmann et al., (1988) J. Mol. Biol. 203, 825) were obtained from Dr. G. Winter (Cambridge, UK). The restriction sites HindIII (HuVhlys) and EcoRV (HuVllys) were introduced to make possible the insertion of the antibody cDNA into the expression vector. Further restriction sites for BanII (HuVhlys) and BstEII or KpnI (HuVllys) were introduced to exchange hypervariable regions en bloc. At the end of the HuVhlys cDNA sequence a stop signal was incorporated. A BanII site in the light chain was removed. These alterations were carried out by means of site directed mutagenesis in the bacteriophage M13mpl18 (Zoller and Smith, Meth. Enzymol. 100, 468–500). The sequence of the completed antibody DNA is shown in Tab. 5 (SEQ ID NOS. 26–29).

For the insertion of the leader sequence $P_1$ (Tab. 4) (SEQ ID NOS. 12–13, 16–18) the modified plasmid pKK233-2 was digested using the restriction enzymes NcoI and PstI, and $P_1$ was inserted in between these sites (pKK233-2-$P_1$). Further cloning steps, apart from the last step, were carried out using the plasmid pUC18. The reason is that the presence of individual parts of the antibody operon in the expression vector adversely influences the growth of the bacterial host.

Before the cloning in pUC18, its BamHI restriction site had to be removed. After digesting with BamHI, the single-stranded ends were filled in using the Klenow fragment and were religated. This modified plasmid was then digested using PstI and HindIII, and $P_2$ (SEQ ID NOS. 14–15, 19–23) plus RBS was ligated in between the restriction sites (pUC18-$P_2$).

During this process, the original HindIII restriction site of the plasmid disappears and a new HindIII restriction site is incorporated. pUC18-$P_2$ was then digested using PstI and HindIII, and the DNA of the heavy chain (PstI-HindIII insert from M13) was ligated into these two sites (pUC18-H$P_2$). This plasmid was then digested using EcoRV and BamHI, and the DNA of the light chain (EcoRV-BamHI insert from M13) was ligated in (pUC18-H$P_2$L).

In a preferred embodiment a Tag sequence was ligated into the new HindIII cleavage site (Tab. 4) (SEQ ID NOS 24–25). The Tag sequence codes for the peptide Glu-Glu-Gly-Glu-Glu-Phe (SEQ ID NO.31) and is recognized by the monoclonal antibody YL 1/2 (Wehland et al. (1984) EMBO J. 3, 1295). The resulting plasmid is pUC-HTP$_2$L.

For the insertion of H$P_2$L or HTP$_2$L into the expression vector, pUC18-H$P_2$L or pUC-HTP$_2$L, respectively, were cut using PstI and BamHI, and the relevant restriction fragment was ligated into these two restriction sites in. the modified plasmid pKK233-2-$P_1$, in each case. A diagrammatic representation of the completed expression vector pFMT is shown in Tab. 6.

Example 2
Isolation of RNA from Human B-lymphocytes

To enrich peripheral B-cells from human blood, this was diluted 1:1 with PBS (phosphate buffered saline) and centrifuged on a cushion of Ficoll® (Pharmacia) (1,077 kg/l). The cells of the interphase were washed twice with PBS and were incubated at 37° C. for one hour on a plastic surface (culture bottle) in RPMI medium containing 10% fetal calf serum. The adherent cells (monocytes and macrophages) adhere to the culture vessel and it was possible in this way to remove them from the preparation. The nonadherent cells were collected by centrifugation and homogenized in 4.4 N guanidinium isothiocyanate, 5% mercaptoethanol and 2% lauroylsarcosine. The homogenate was then centrifuged on a cushion of 5.7 M CsCl at 125,000 g for 18 hours. The sedimented RNA was dissolved in double-distilled $H_2O$ and precipitated at −20° C. overnight using 70% ethanol and 1/20 volume of 8M LiCl.

In order to obtain an even larger variety of antibodies of different specificities, RNA preparations of, in each case, 500 ml of the blood from 20 different people were mixed.

Example 3
Amplification of Antibody DNA

The mRNA was purified on oligo-dT-Sepharose (kit supplied by Pharmacia) and translated into the cDNA by means of reverse transcriptase (kit supplied by Amersham) and oligo-dT primer. The products were used directly in the polymerase chain reaction (PCR). PCR primers and hybridization sites are shown in Tab. 1(SEQ ID NOS. 1–11) and 2. Two different expression banks were produced by combining the $\mu$-DNA obtained with either kappa- or lambda-DNA in the vector pFMT. The use of different primers for the synthesis of the noncoding strands in the polymerase chain reaction makes possible the preparation of two different antibody types which contain, in one case, only the variable domain and, in the other case, additionally a constant domain (similar to the Fab fragment of an antibody). For the PCR, 4 μl of a cDNA synthesis were reacted with 0.2 nmol of each of the two primers in a volume of 50 μl. The reaction mixture contained 100 mM KCl, 0.1% gelatin and 2.5 U of Taq polymerase. After 30 polymerization cycles comprising 1 min at 95° C., 2 min at 55° C. and 2 min at 72° C., the DNA was precipitated using ethanol.

Example 4

Insertion of the Antibody DNA into the Expression Plasmid

The precipitated DNA was taken up in application buffer for agarose gel (0.1% bromophenol blue, 7% Ficoll® [Pharmacia]) and fractionated in TBE buffer (45 mM tris/borate pH 8.0, 10 mM EDTA) on 2% agarose at 10V/cm. The antibody DNA synthesized was identified by means of its molecular weight and eluted from the gel. It was precipitated using ethanol and then taken up in buffer for the particular restriction enzymes and cut with the appropriate (cf. Tab. 1(SEQ ID NOS. 1–11) and 2) restriction enzymes (Boehringer Mannheim). After precipitation in ethanol, it was ligated into the vector pFMT cut in the same way, as is shown in the form of a diagram in Tab. 7.

Example 5

Expression and Screening Antibodies in *E. coli*

Competent *E. coli* are transfected with pFMT plasmids containing the inserted antibody-DNA library, grown on agarose plates and then incubated using nitrocellulose filters coated with the desired antigen. After removing non-specifically bound antibodies, the active clones are identified with a labeled antibody against the human immunoglobulins secreted from *E. coli*. In the preferred embodiment, the monoclonal antibody YL 1/2 which is directed against the Tag sequence is used to identify the desired clones.

BRIEF DESCRIPTION OF THE DRAWINGS

Restriction map of the expression vector pKK233-2 (Amann and Brosius, loc. cit.).

Ptrc denotes hybrid tryptophan lac promoter

RBS denotes ribosome binding site rrnB denotes ribosomal RNA B (5S RNA)

5S denotes gene for 5S RNA (contains rrnB)

Before cloning antibody DNA in the expression vector, the following alterations were carried out:

1) The SalI and EcoRI restriction sites were removed together with the DNA between them.
2) The HindIII restriction site was converted into a BamHI restriction site.

TABLE 1

Oligonucleotide primers for the amplification of cDNA using the polymerase chain reaction.

1. Oligonucleotide primers for the forward PCR

D. μchain (SEQ ID NO:1)

```
        PstI
GAGGTGCAGCTGCAGGAGTCTGGGGGAGGCTT
```

E. kappa-chain (SEQ ID NO:2)

```
                    BstEII
TGTCTGCATCTGT(A/G)GGAGACAGGGTCACCATCA(A/C)TTG
```

F. λchain (SEQ ID NO:3)

```
                              BstEII
CCTCAG(C/T)GTCTGGG(A/T)CCCCAGGACAGAGGGTGACCATCTCCTGC
```

2. Oligonucleotide primers for the backward PCR (variable domain plus adjacent constant domain)

A1. μchain (without Tag sequences) (SEQ ID NO:4)

```
                HindIII
GGGTGGGACGAAGAAGCTTACTTAGGGAGGCAGCTCAGCAATCAC
```

A2. μchain (with Tag sequences) (SEQ ID NO:5)

```
                    HindIII
GGGTGGGACGAAGAAGCTAAGCTTGGGAGGCAGCTCAGCAATCAC
```

B. κchain (SEQ ID NO:6)

```
          Bam HI
GGCACTTCGGATCCTAACACTCTCCCCTGTTGAAGCTCTTTGTGACGGGCGA

GCTCAGGCC
```

C. λchain (SEQ ID NO:7)

```
              Bam HI
GTGAGGG(A/T)TGGGGATCCTATGAACATTCTGTAGGGCCACTGT
```

TABLE 1-continued

3. Oligonucleotide primers for the backward PCR (variable domain)

G1.μchain (without Tag sequences)  (SEQ ID NO:8)

```
           HindIII
CACAGGAGACGAGGGGGAAAAGCTTTGGGGCTTATGCACTCCC
```

G2.μchain (with Tag sequences)  (SEQ ID NO:9)

```
           HindIII
CACAGGAGACGAGGGGGAAAAGCTTTGGGGCGGATGCACTCCC
```

H. κchain  (SEQ ID NO:10)

```
      Bam HI
AACAGAGGCGGATCCTCATTTCAACTGCTCATCAGATGGCGGGAAGATGAA
GAC
```

I. λchain  (SEQ ID NO:11)

```
                Bam HI
AGCTCCTCAGAGGA(C/G)GGCGGGATCCGAGTGACCTAGGGG
```

TABLE 2

Positions of the primers for the polymerase chain reaction (PCR) of antibody DNA.

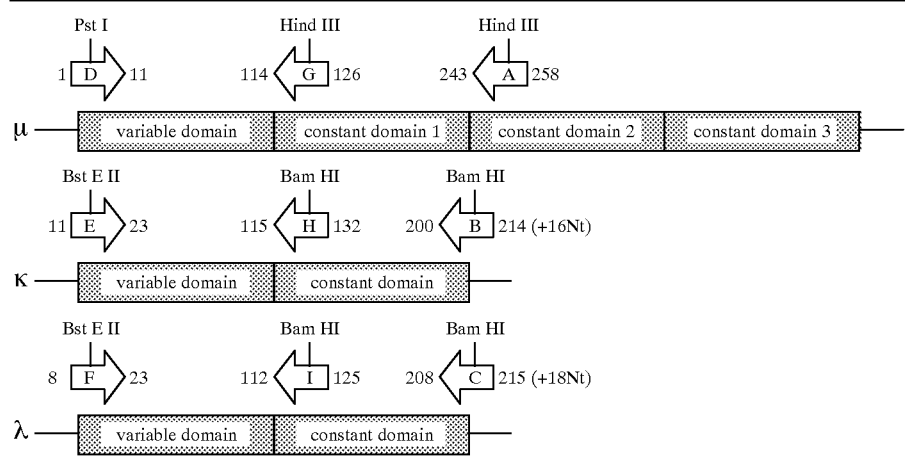

The individual experiences are listed in Tab. 1. The numbers indicate the position of the amino acids from which the particular primers are derived.

TABLE 3

CONSTRUCTION OF THE VECTOR pFMT FOR THE EXPRESSION AND SECRETION OF ANTIBODIES IN BACTERIA
DNA OF THE VARIABLE DOMAIN OF A HUMAN LYSOZYME ANTIBODY
↓
INTRODUCTION OF RESTRICTION SITES BY SITE DIRECTED MUTAGENESIS
↓
SYNTHESIS OF THE LEADER SEQUENCE OF PECTATE LYASE AND OF THE RIBOSOME BINDING SITE
↓
LIGATION INTO BACTERIAL EXPRESSION PLASMIDS

TABLE 3-continued

↓

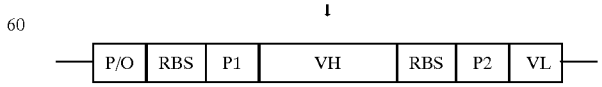

P/O: promoter/operator, RBS: ribosome binding site, P2: leader sequence of pectate lyase, VH: variable domain of the heavy chain, VL: variable domain of the light chain

TABLE 4

Sequences of the leader sequences P1 and P2 in the antibody operon, and of the Tag sequences

P1

Leader sequence of pectate lyase (P1) (SEQ ID NOS:12—13)

```
  M   K   Y   L   L   P   T   A   A   A   G   L   L   L   L   A   A   Q   P   A   M   A   Q   V   Q   L   Q
CATGAAATACCTCTTGCCTACGGCAGCCGCTGGCTTGCTGCTGCTGGCAGCTCAGCCGGCGATGGCGCAAGTTCAGCTGCA(G)
                                                                                    PstI
```

P2

```
                                    Leader sequence of pectate                        (SEQ ID NOS:14—15)
                      RBS           lyase (P2)
                                      M   K   Y   L   L   P   T   A   A   A
(C)TGCAGCCAAGCTTGAATTCATTAAAGAGGAGAAATTAACTCCATGAAGTACTTACTGCCGACCGCTGCGGCG
   PstI    HindIII
```

```
  G   L   L   L   L   A   A   Q   P   A   M   A   D   I
GGTCTCCTGCTGTTGGCGGCTCAGCCGGCTATGGCTGATATCGGATCCAGCT
                                       EcoRV   BamHI
```

The nucleotides in parenthesis are the adjacent nucleotides of the plasmid.

The leader sequences were synthesized by hybridization of the following oligonucleotides

P1 a. 5'CATGAAATACCTCTTGCCTACGGCAGCCGCTGGCTTG3' (SEQ ID NO:16)

b. 3'TTTATGGAGAACGGATGCCGTCGGCGACCGAACGACGACGACCGTCGAGTCGGCCGCTACCGCGTTCAAGTCG5' (SEQ ID NO:17)

c. 5'CTGCTGCTGGCAGCTCAGCCGGCGATGGCGCAAGTTCAGCTGCA3' (SEQ ID NO:18)

P2 a. 5'GCCAAGCTTGAATTCATTAAAGAGGAGAAA3' (SEQ ID NO:19)

b. 5'TTAACTCCATGAAGTACTTACTGCCGACCGCTGCG3' (SEQ ID NO:20)

c. 3'ACGTCGGTTCGAACTTAAGTAATTTCTCCTCTTTAATTGAGGTACTTCATGAATGACGGCGACGCCGCCCAGAGGA (SEQ ID NO:21)

CGACAACCGCCGAGTCGGCCGATACCGACTATAGCCTAGGTCGA5' d. 5'GCTCAGCCGGCTATGGCTGATATCGGATCC3' (SEQ ID NO:22)

e. 5'GCGGGTCTCCTGCTGTTGGCG3' (SEQ ID NO:23)

The Tag sequences were synthesized by the hybridization of the following sequences:

a. 5'AGCTTGAAGAAGGTGAAGAATTCTAATG3' (SEQ ID NO:24)

b. 5'AGCTCATTAGAATTCTTCACCTTCTTCA3' (SEQ ID NO:25)

TABLE 5

Nucleotide sequences of antibody DNA a) Heavy chain (variable domain), HuVhlye (SEQ ID NOS. 26—27) HindIII.......

TABLE 5-continued

Nucleotide sequences of antibody DNA

```
                I                         10
..........G  V  H  S  Q  V  Q  L  Q  E  S  G  P  G  L  V  R.
CTCTCCACAGGTGTCCACTCCCAGGTCCAACTGCAGGAGAGCGGTCCAGGTCTTGTGAGA
                          PszI

20       I                      30      CDR1
 .P  S  Q  T  L  S  L  T  C  T  V  S  G  F  T  F  S /G//Y//G/
CCTAGCCAGACCCTGAGCCAGACCTGCACCCTGTCTGGCTTCACCTTCAGCGGCTATGGT
                    BrpMI 40                        50
/V/N/ W  V  R  Q  P  P  G  R  G  L  E  W  I  G /M/ I/ W/G/
GTAAACTGGGTGAGACAGCCACCTGGACGAGGTCTTGAGTGGATTGGAATGATTTGGGGT
                                              BrpMI

CDR2                   60                     70
/D/ G/ N/ T/ D/ Y/ N/ S/ A/ L/ X/ S  R  V  T  M  L  V  D  T
GATGGAAACACAGACTATAATTCAGCTCTCAAATCCAGAGTGACAATGCTGGTAGACACC 80                       90
 S  K  N  Q  F  S  L  R  L  S  S  V  T  A  A  D  T  A  V  Y
AGCAAGAACCAGTTCAGCCTGAGACTCAGCAGCGTGACAGCCGCCGACACCGCGGTCTAT
                                                SacII

100  CDR3                   110
 Y  C  A  R /E/ R/ D/ Y/ R/ L/ D/ Y  W  G  Q  G  S  L  V  T
TATTGTGCAAGAGAGAGAGATTATAGGCTTGACTACTGGGGTCAGGGCTCCCTCGTCACA
                                           BanII

V  S  S  Stop
GTCTCCTCATAAGCCTCCTTACAACCCCTCTCTTCTATTCAGCTTAA..........BamHI
         HindIII b) Light chain (variable domain), HuVllys (SEQ ID NOS. 28-29)

1                         10
         G  V  E  S  D  I  Q  N  T  Q  S  P  S  S  L  S  A.
CTCTCCACAGGTGTCCACTCCGATATCCAGATGACCCAGAGCCCAAGCAGCCTGAGGGCC
                     EcoRV

20                    CDR1       30
 .S  V  G  D  R  V  T  I  T  C /R/ A/ S/ G/ N/ I/ E/ N/ Y/ D/
AGCGTGGGTGACAGGGTGACCATCACCTGTAGAGCCAGCGGTAACATCCACAACTACCTG
                BstEII 40                         50     CDR2
/A/ W  Y  Q  Q  K  P  G  K  A  F  K  L  L  I  Y /Y/ T/ T/ T/
GCTTGGTACCAGCAGAAGCCAGGTAAGGCCTCCAAAGCTGGTGATCTACTACACCACCACC 60                        70
/L/ A/ D/ G  V  P  S  R  F  S  G  S  G  S  G  T  D  T  T  T
CTGGCTGACGGTGTGCCAAGCAGATTCAGCGGTAGCGGTAGCGGTACCGACTTCACCTTC 80                       90      CDR3
 .T  I  S  S  L  Q  P  E  D  I  A  T  Y  Y  C /Q/ E/ T/ W/ S
ACCATCAGCAGCCTCCAGCCAGAGGACATCGCCACCTACTACTGCCAGCAGTTCTGGAGC

100
/T/ P/ R/ T/ F  G  Q  G  T  K  V  I  I  K  R..I Stop
ACCCCAAGGACGTTCGGCCAAGGTACCAAGGTGGAAATCAAACGTGAGTAGAATTTAAAC
                         KpaI TTTGCTTCCTCAGTTGGATCC
             BamHI
```

TABLE 6
The Antibody Expression Plasmid pFMT
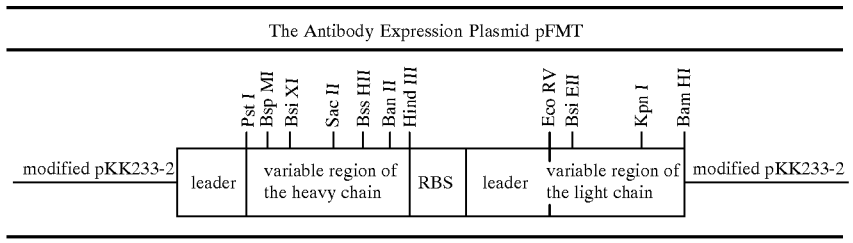
There is an RBS in the plasmid upstrem of the heavy chain part but it is not drawn in here.
TABLE 7
Insertion of the antibody libraries in the expression vector pFMT
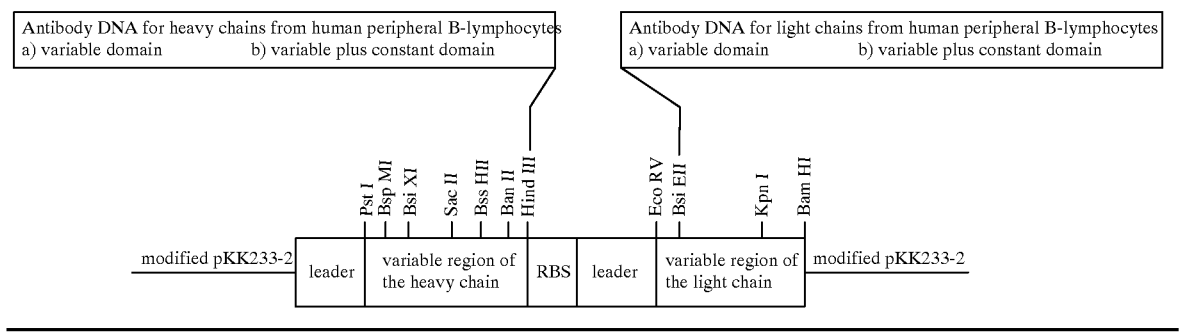

What is claimed is:

1. A human-antibody library obtained by means of transcription of isolated mRNA from peripheral non-activated human B-lymphocytes into cDNA, subsequent amplification of cDNA coding for antibodies by polymerase chain reaction (PCR) by means of suitable IgM-specific primers, and subsequent incorporation in suitable expression plasmids and finally expression, in individual clones, of the relevant antibody RNA which is contained therein and has been amplified in cDNA.

2. A human-antibody library as claimed in claim 1, wherein the expression takes place in the plasmid pFMT.

3. A human-antibody library as claimed in claim 1, wherein,
   by selecting suitable primers,
      (a.) only the variable region, or
      (b.) a constant domain plus the variable region
   is amplified in each clone.

4. A human-antibody library as claimed in claim 2, wherein,
   by selecting suitable primers,
      (a.) only the variable region, or
      (b.) a constant domain plus the variable region
   is amplified in each clone.

5. A process for preparing a human-antibody library, which comprises mRNA being isolated from non-activated peripheral human B-lymphocytes and being transcribed into cDNA, subsequently amplifying the cDNA coding for antibodies by PCR by means of suitable IgM-specific primers, then carrying out an incorporation into suitable expression plasmids and finally expressing the antibody cDNA in individual clones.

6. The process as claimed in claim 5, wherein the expression takes place in plasmid pFMT.

7. The process as claimed in claim 5, wherein by selecting suitable primers, only the variable region or a constant domain plus the variable region is amplified in each case.

8. The process as claimed in claim 6, wherein by selecting suitable primers, only the variable region or a constant domain plus the variable region is amplified in each case.

9. A human antibody library comprising recombinant DNA molecules coding for antibodies wherein said DNA molecules are obtained by means of transcription of isolated mRNA from non-activated peripheral human B lymphocytes into cDNA, amplification of said cDNA by polymerase chain reaction using IgM specific primers and incorporation into a suitable expression vector.

10. The human antibody library as claimed in claim 9 wherein at least one of the IgM specific primers is selected from the group consisting of nucleotide SEQ ID NOS.: 1, 2, 3, 4, 5, 6, 7, 8, 9, 10 and 11.

11. A method of obtaining a human antibody library comprising:
   a) obtaining isolated mRNA from non-activated human peripheral B-lymphocytes,
   b) transcribing said mRNA into cDNA,
   c) amplifying cDNA coding for antibodies by polymerase chain reaction using IgM-specific primers,
   d) incorporating said amplified DNA into a suitable expression vector, and
   e) expressing said incorporated DNA in individual clones.

12. The method of obtaining a human antibody library as claimed in claim 11 wherein the mRNA is obtained from a preparation of lymphocytes enriched for B-cells.

13. The method obtaining a human antibody library as claimed in claim 11 wherein a mixture of B-lymphocytes are obtained from different individuals.

14. A method of obtaining a human antibody library as claimed in claim 11 wherein at least one of the primers used for amplifying the DNA are selected from the group consisting of nucleotide SEQ ID NOS.: 1, 2, 3, 4, 5, 6, 7, 8, 9, 10, and 11.

15. A process for isolating human antibodies specific for a selected antigen, comprising screening human-antibody libraries as claimed in claim 1 for antibodies that specifically bind to the selected antigen.

16. The antibody expression plasmid pFMT.

* * * * *

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GAGGTGCAGC TGCAGGAGTC TGGGGGAGGC TT                              32
```

(2) INFORMATION FOR SEQ ID NO:2:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
TGTCTGCATC TGTRGGAGAC AGGGTCACCA TCAMTTG                         37
```

(2) INFORMATION FOR SEQ ID NO:3:

(i) SEQUENCE CHARACTERISTICS:
      (A) LENGTH: 44 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

```
CCTCAGYGTC TGGGWCCCCA GGACAGAGGG TGACCATCTC CTGC                 44
```

(2) INFORMATION FOR SEQ ID NO:4:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

```
GGGTGGGACG AAGAAGCTTA CTTAGGGAGG CAGCTCAGCA ATCAC                45
```

(2) INFORMATION FOR SEQ ID NO:5:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:5:

GGGTGGGACG AAGAAGCTAA GCTTGGGAGG CAGCTCAGCA ATCAC          45

(2) INFORMATION FOR SEQ ID NO:6:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGCACTTCGG ATCCTAACAC TCTCCCCTGT TGAAGCTCTT TGTGACGGGC GAGCTCAGGC          60

C          61

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTGAGGGWTG GGATCCTATG AACATTCTGT AGGGGCCACT GT          42

(2) INFORMATION FOR SEQ ID NO:8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CACAGGAGAC GAGGGGGAAA AGCTTTGGGG CTTATGCACT CCC          43

(2) INFORMATION FOR SEQ ID NO:9:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CACAGGAGAC GAGGGGGAAA AGCTTTGGGG CGGATGCACT CCC          43

(2) INFORMATION FOR SEQ ID NO:10:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AACAGAGGCG GATCCTCATT TCAACTGCTC ATCAGATGGC GGGAAGATGA AGAC          54

(2) INFORMATION FOR SEQ ID NO:11:

(i) SEQUENCE CHARACTERISTICS:
          (A) LENGTH: 39 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:11:

AGCTCCTCAG AGGASGGCGG GATCCGAGTG ACCTAGGGG                         39

(2) INFORMATION FOR SEQ ID NO:12:

(i) SEQUENCE CHARACTERISTICS:
          (A) LENGTH: 27 amino acids
          (B) TYPE: amino acid
          (D) TOPOLOGY: linear (ii) MOLECULE TYPE: protein (xi) SEQUENCE DESCRIPTION: SEQ ID NO:12:

Met Lys Tyr Leu Leu Pro Thr Ala Ala Ala Gly Leu Leu Leu Leu Ala
 1               5                  10                  15

Ala Gln Pro Ala Met Ala Gln Val Gln Leu Gln
            20                  25

(2) INFORMATION FOR SEQ ID NO:13:

(i) SEQUENCE CHARACTERISTICS:
          (A) LENGTH: 82 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: CDS
          (B) LOCATION: 2..82

(xi) SEQUENCE DESCRIPTION: SEQ ID NO:13:

C ATG AAA TAC CTC TTG CCT ACG GCA GCC GCT GGC TTG CTG CTG CTG     46
  Met Lys Tyr Leu Leu Pro Thr Ala Ala Ala Gly Leu Leu Leu Leu
   1               5                  10                  15

GCA GCT CAG CCG GCG ATG GCG CAA GTT CAG CTG CAG                   82
Ala Ala Gln Pro Ala Met Ala Gln Val Gln Leu Gln
            20                  25

(2) INFORMATION FOR SEQ ID NO:14:

(i) SEQUENCE CHARACTERISTICS:
          (A) LENGTH: 24 amino acids
          (B) TYPE: amino acid
          (D) TOPOLOGY: linear (ii) MOLECULE TYPE: protein (xi) SEQUENCE DESCRIPTION: SEQ ID NO:14:

Met Lys Tyr Leu Leu Pro Thr Ala Ala Ala Gly Leu Leu Leu Leu Ala
 1               5                  10                  15

Ala Gln Pro Ala Met Ala Asp Ile
            20

(2) INFORMATION FOR SEQ ID NO:15:

(i) SEQUENCE CHARACTERISTICS:
            (A) LENGTH: 125 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 44..115

(xi) SEQUENCE DESCRIPTION: SEQ ID NO:15:

CTGCAGCCAA GCTTGAATTC ATTAAAGAGG AGAAATTAAC TCC ATG AAG TAC TTA        55
                                               Met Lys Tyr Leu
                                                 1

CTG CCG ACC GCT GCG GCG GGT CTC CTG CTG TTG GCG GCT CAG CCG GCT       103
Leu Pro Thr Ala Ala Ala Gly Leu Leu Leu Leu Ala Ala Gln Pro Ala
  5                  10                  15                  20

ATG GCT GAT ATC GGATCCAGCT                                            125
Met Ala Asp Ile (2) INFORMATION FOR SEQ ID NO:16:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

CATGAAATAC CTCTTGCCTA CGGCAGCCGC TGGCTTG                               37

(2) INFORMATION FOR SEQ ID NO:17:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

GCTGAACTTG CGCCATCGCC GGCTGAGCTG CCAGCAGCAG CAAGCCAGCG GCTGCCGTAG       60

GCAAGAGGTA TTT                                                         73

(2) INFORMATION FOR SEQ ID NO:18:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

CTGCTGCTGG CAGCTCAGCC GGCGATGGCG CAAGTTCAGC TGCA                        44

(2) INFORMATION FOR SEQ ID NO:19:

(i) SEQUENCE CHARACTERISTICS:
            (A) LENGTH: 30 base pairs
            (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:19:

GCCAAGCTTG AATTCATTAA AGAGGAGAAA                                           30

(2) INFORMATION FOR SEQ ID NO:20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TTAACTCCAT GAAGTACTTA CTGCCGACCG CTGCG                                     35

(2) INFORMATION FOR SEQ ID NO:21:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

AGCTGGATCC GATATCAGCC ATAGCCGGCT GAGCCGCCAA CAGCAGGAGA CCCGCCGCAG          60

CGGTCGGCAG TAAGTACTTC ATGGAGTTAA TTTCTCCTCT TAATGAATT CAAGCTTGGC          120

TGCA                                                                     124

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GCTCAGCCGG CTATGGCTGA TATCGGATCC                                           30

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GCGGGTCTCC TGCTGTTGGC G                                                    21

(2) INFORMATION FOR SEQ ID NO:24:

(i) SEQUENCE CHARACTERISTICS:
        (A) LENGTH: 28 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:24:

AGCTTGAAGA AGGTGAAGAA TTCTAATG                                        28

(2) INFORMATION FOR SEQ ID NO:25:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

AGCTCATTAG AATTCTTCAC CTTCTTCA                                        28

(2) INFORMATION FOR SEQ ID NO:26:

(i) SEQUENCE CHARACTERISTICS:
            (A) LENGTH: 120 amino acids
            (B) TYPE: amino acid
            (D) TOPOLOGY: linear (ii) MOLECULE TYPE: protein (xi) SEQUENCE DESCRIPTION: SEQ ID NO:26:

Gly Val His Ser Gln Val Gln Leu Gln Glu Ser Gly Pro Gly Leu Val
 -4           1               5                  10

Arg Pro Ser Gln Thr Leu Ser Leu Thr Cys Thr Val Ser Gly Phe Thr
           15                  20                  25

Phe Ser Gly Tyr Gly Val Asn Trp Val Arg Gln Pro Pro Gly Arg Gly
       30                  35                  40

Leu Glu Trp Ile Gly Met Ile Trp Gly Asp Gly Asn Thr Asp Tyr Asn
 45                  50                  55                  60

Ser Ala Leu Lys Ser Arg Val Thr Met Leu Val Asp Thr Ser Lys Asn
               65                  70                  75

Gln Phe Ser Leu Arg Leu Ser Ser Val Thr Ala Ala Asp Thr Ala Val
           80                  85                  90

Tyr Tyr Cys Ala Arg Glu Arg Asp Tyr Arg Leu Asp Tyr Trp Gly Gln
           95                 100                 105

Gly Ser Leu Val Thr Val Ser Ser
       110                 115

(2) INFORMATION FOR SEQ ID NO:27:

(i) SEQUENCE CHARACTERISTICS:
            (A) LENGTH: 407 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 10..369

(ix) FEATURE:
            (A) NAME/KEY: sig_peptide
            (B) LOCATION: 10..21

(ix) FEATURE:
    (A) NAME/KEY: mat_peptide
    (B) LOCATION: 22..369

(xi) SEQUENCE DESCRIPTION: SEQ ID NO:27:

```
CTCTCCACA GGT GTC CAC TCC CAG GTC CAA CTG CAG GAG AGC GGT CCA              48
          Gly Val His Ser Gln Val Gln Leu Gln Glu Ser Gly Pro
           -4           1               5

GGT CTT GTG AGA CCT AGC CAG ACC CTG AGC CTG ACC TGC ACC GTG TCT            96
Gly Leu Val Arg Pro Ser Gln Thr Leu Ser Leu Thr Cys Thr Val Ser
 10              15                  20                  25

GGC TTC ACC TTC AGC GGC TAT GGT GTA AAC TGG GTG AGA CAG CCA CCT           144
Gly Phe Thr Phe Ser Gly Tyr Gly Val Asn Trp Val Arg Gln Pro Pro
                 30                  35                  40

GGA CGA GGT CTT GAG TGG ATT GGA ATG ATT TGG GGT GAT GGA AAC ACA           192
Gly Arg Gly Leu Glu Trp Ile Gly Met Ile Trp Gly Asp Gly Asn Thr
             45                  50                  55

GAC TAT AAT TCA GCT CTC AAA TCC AGA GTG ACA ATG CTG GTA GAC ACC           240
Asp Tyr Asn Ser Ala Leu Lys Ser Arg Val Thr Met Leu Val Asp Thr
         60                  65                  70

AGC AAG AAC CAG TTC AGC CTG AGA CTC AGC AGC GTG ACA GCC GCC GAC           288
Ser Lys Asn Gln Phe Ser Leu Arg Leu Ser Ser Val Thr Ala Ala Asp
     75                  80                  85

ACC GCG GTC TAT TAT TGT GCA AGA GAG AGA GAT TAT AGG CTT GAC TAC           336
Thr Ala Val Tyr Tyr Cys Ala Arg Glu Arg Asp Tyr Arg Leu Asp Tyr
 90                  95                 100                 105

TGG GGT CAG GGC TCC CTC GTC ACA GTC TCC TCA TAAGCTTCCT TACAACCTCT         389
Trp Gly Gln Gly Ser Leu Val Thr Val Ser Ser
                 110                 115

CTCTTCTATT CAGCTTAA                                                       407
```

(2) INFORMATION FOR SEQ ID NO:28:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:28:

```
Gly Val His Trp Asp Ile Gln Met Thr Gln Ser Pro Ser Ser Leu Ser
 -4           1               5                  10

Ala Ser Val Gly Asp Arg Val Thr Ile Thr Cys Arg Ala Ser Gly Asn
         15                  20                  25

Ile His Asn Tyr Leu Ala Trp Tyr Gln Gln Lys Pro Gly Lys Ala Pro
     30                  35                  40

Lys Leu Leu Ile Tyr Tyr Thr Thr Thr Leu Ala Asp Gly Val Pro Ser
 45                  50                  55                  60

Arg Phe Ser Gly Ser Gly Ser Gly Thr Asp Phe Thr Phe Thr Ile Ser
                 65                  70                  75

Ser Leu Gln Pro Glu Asp Ile Ala Thr Tyr Tyr Cys Gln His Phe Trp
         80                  85                  90

Ser Thr Pro Arg Thr Phe Gly Gln Gly Thr Lys Val Glu Ile Lys Arg
     95                 100                 105

Glu
```

(2) INFORMATION FOR SEQ ID NO:29:

(i) SEQUENCE CHARACTERISTICS:

(A) LENGTH: 381 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 10..348

(ix) FEATURE:
        (A) NAME/KEY: sig_peptide
        (B) LOCATION: 10..21

(ix) FEATURE:
        (A) NAME/KEY: mat_peptide
        (B) LOCATION: 22..348

(xi) SEQUENCE DESCRIPTION: SEQ ID NO:29:

```
CTCTCCACA GGT GTC CAC TGG GAT ATC CAG ATG ACC CAG AGC CCA AGC            48
          Gly Val His Trp Asp Ile Gln Met Thr Gln Ser Pro Ser
           -4               1               5

AGC CTG AGC GCC AGC GTG GGT GAC AGG GTG ACC ATC ACC TGT AGA GCC          96
Ser Leu Ser Ala Ser Val Gly Asp Arg Val Thr Ile Thr Cys Arg Ala
 10              15                  20                  25

AGC GGT AAC ATC CAC AAC TAC CTG GCT TGG TAC CAG CAG AAG CCA GGT         144
Ser Gly Asn Ile His Asn Tyr Leu Ala Trp Tyr Gln Gln Lys Pro Gly
                 30                  35                  40

AAG GCT CCA AAG CTG CTG ATC TAC TAC ACC ACC ACC CTG GCT GAC GGT         192
Lys Ala Pro Lys Leu Leu Ile Tyr Tyr Thr Thr Thr Leu Ala Asp Gly
             45                  50                  55

GTG CCA AGC AGA TTC AGC GGT AGC GGT AGC GGT ACC GAC TTC ACC TTC         240
Val Pro Ser Arg Phe Ser Gly Ser Gly Ser Gly Thr Asp Phe Thr Phe
             60                  65                  70

ACC ATC AGC AGC CTC CAG CCA GAG GAC ATC GCC ACC TAC TAC TGC CAG         288
Thr Ile Ser Ser Leu Gln Pro Glu Asp Ile Ala Thr Tyr Tyr Cys Gln
         75                  80                  85

CAC TTC TGG AGC ACC CCA AGG ACG TTC GGC CAA GGT ACC AAG GTG GAA         336
His Phe Trp Ser Thr Pro Arg Thr Phe Gly Gln Gly Thr Lys Val Glu
 90                  95                 100                 105

ATC AAA CGT GAG TAGAATTTAA ACTTTGCTTC CTCAGTTGGA TCC                    381
Ile Lys Arg Glu
```

(2) INFORMATION FOR SEQ ID NO:30:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
TTGACAATTA ATCATCCGGC TCGTATAATG TGTGGAATTG TGAGCGGATA ACAATTTCAC        60

ACAGGAAACA GACCATGGCT GCAGCCAAGC TTGGCTGTTT TGGC                       104
```

(2) INFORMATION FOR SEQ ID NO:31:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Glu Glu Gly Glu Glu Phe
1               5